United States Patent [19]

Kaestle

[11] Patent Number: 5,058,588
[45] Date of Patent: Oct. 22, 1991

[54] OXIMETER AND MEDICAL SENSOR THEREFOR
[75] Inventor: Siegfried Kaestle, Nufringen, Fed. Rep. of Germany
[73] Assignee: Hewlett-Packard Company, Palo Alto, Calif.
[21] Appl. No.: 409,547
[22] Filed: Sep. 19, 1989
[51] Int. Cl.[5] .............................................. A61B 5/00
[52] U.S. Cl. ...................................... 128/633; 356/41
[58] Field of Search ........................... 128/633; 356/41
[56] References Cited

U.S. PATENT DOCUMENTS 4,700,708  10/1987  New, Jr. et al. ..................... 128/633
4,805,623   2/1989  Jobsis ................................. 128/633
4,942,877   7/1990  Sakai et al. .......................... 128/633

FOREIGN PATENT DOCUMENTS

63-63430   3/1988  Japan .................................. 128/633

Primary Examiner—William E. Kamm
Assistant Examiner—Kevin Pontius
Attorney, Agent, or Firm—Richard Schuette

[57] ABSTRACT

A medical sensor for measuring oxygen saturation contains encoding means for encoding the type of sensor. An oximeter comprises corresponding decoding means. The type of sensor represents the place of application at the human body. The oximeter uses this information to calculate oxygen saturation in dependence the place of application and for further purposes.

3 Claims, 7 Drawing Sheets

OXIMETER AND MEDICAL SENSOR THEREFOR

BACKGROUND OF THE INVENTION

This invention relates to an oximeter and a medical sensor therefor, said medical sensor comprising light emitting means for emitting light into the tissue of a patient, light receiving means for receiving the light transmitted through or reflected by said tissue, and connection means for the connection of said medical sensor to said oximeter.

Pulse oximetry is a non-invasive technique to evaluate the condition of a patient. Usually, a sensor or a probe comprises light emitting means such as light-emitting diodes (LEDs). Two or more of these LEDs with different wavelengths (e.g. red and infrared) may be used. The emitted light is directed into the tissue of the patient, and light receiving means such as photodiodes or phototransistors measure the amount of transmitted or reflected light. In the case of transmission measurement, the transmitter and receiver diodes are arranged opposite to each other with respect to the human tissue, whereas in the case of reflection measurement, they are arranged on the same side of the tissue.

The measured intensity can be used to calculate the oxygen saturation in the arterial blood of the patient if measured at at least two wavelengths. has been described in detail in a lot of former publications. A rather good breakdown of the theory is e.g. contained in European Patent Application EP-A-262 778.

Usually, the sensor detachably connected to the oximeter comprises at least two LEDs emitting light of a wavelength of e.g. 650 nm (Nanometers)—red—and 1000 nm—infrared. The intensity of the emitted light can be modulated by the oximeter in that the exciting current of the LEDs is varied. The photocurrent received by the receiving element is measured by the oximeter and used to calculate the oxygen saturation of the arterial blood.

It is important that the wavelength of the emitting diodes is well-known as the used wavelengths directly influence the results of the calculation. U.S. Pat. Nos. 4,621,643, 4,700,708 and 4,770,179 therefore propose to use an encoding element, usually a resistor, implemented in the sensor to encode the wavelengths. The oximeter decodes the value and selects appropriate extinction coefficients for oxygen saturation calculation.

It has been found that such encoding does, under some particular circumstances, not lead to sufficiently accurate measuring results. In particular, the oxygen saturation calculated by means of said extinctions coefficients according to Lambert-Beer's law is based on an ideal optical model and has to be corrected empirically, i.e. by comparative measurements with a lot of patients. The inventor has noted that major reasons that the ideal model does not comply with practical measurements are:

1. Light is scattered by blood corpuscles;
2. The medium (human tissue) has inhomogeneous characteristics;
3. different paths for the light beams emitted by the various light sources (the light-emitting diodes are not located at the same place, and light refraction is not identical);
4. Due to the pressure exerted by the sensor, venous pulsations of the tissue are also recorded;
5. The light-emitting diodes do not have exactly monochromatic characteristics.

The differences between the theoretically calculated oxygen saturation value and the real value are considerable, e.g. approx. factor 2 for an oxygen saturation of 50%. This problem affects the accuracy of an oximeter.

BRIEF DESCRIPTION OF THE INVENTION

It is therefore a major objective of the present invention to provide an oximeter and a sensor therefor which allow to calculate and display oxygen saturation with a better accuracy.

According to a first aspect of the invention, this problem is solved in that the medical sensor further comprises means for encoding the type of sensor among a multiplicity of various sensors connectable to the oximeter.

Various tests carried out by the inventor revealed that the deviations between the theoretical and the real oxygen saturation value are primarily influenced by the place of application of the sensor. It has been found that the human tissue at various places of sensor application has different texture influencing the interrelation between theoretically calculated and real oxygen saturation value.

Known oximeters allow the connection of sensors of different types, i.e. for application at various parts of the human body. For example, sensors are available for application at the finger, the ear, the foot or arm (for neonates) etc. Still the influence of the place of application is not taken into account, i.e. if any correction of the theoretically calculated value is done at all, the correction process is the same regardless of the kind of sensor, i.e. its place of application.

It is a major contribution of the present invention that the inventor has recognized the role of the place of application. The invention therefore proposes to use encoding means comprised in the sensor to encode the type of sensor among a multiplicity of sensors. As each of these various types of sensors is intended for application at a specific part of the human body (and can—due to its mechanical properties—only be applied to this specific part), this is an indirect encoding of the place of application. The information may be used by the oximeter to select a specific one among a variety of correction algorithms to correct the theoretically calculated oxygen saturation value in dependence of the place of sensor application. The information may also be directly used for oxygen saturation calculation. This results in an oxygen saturation value of improved accuracy.

As already outlined, said encoding means may be used to make a distinction between a finger sensor, an ear sensor, a foot sensor and an arm sensor. The information on the kind of applied sensor may also be used for further purposes: As each sensor has a specific, predefined number of LEDs, the oximeter is able to test these and to generate a (technical) alarm if one of these LEDs fails. No false alarms are generated if, for example, a specific sensor contains 3 LEDs and another contains 2 of them. According to a preferred embodiment of the invention, the encoding means may also be directly representative to the number of light emitting diodes.

Another feature of sensor recognition is that the maximum driving current can be adapted to the sensor in use.

A further feature is that the contact between sensor and human tissue, i.e. sensor fastening, can be tested by means of an attenuation measurement. As the attenuation characteristics of sensors of different kind is also different, such a test can only be performed and evaluated if the type of sensor is known to the oximeter.

As some kind of by-product, the inventive encoding technique may also be used to distinguish between sensors of the transmission type and of the reflection type. Further, it can be recognized to which kind of human being the sensor is applied, e.g. adults/neonates (The kind of human being also influences the correction to be performed on the theoretical oxygen saturation value or for directly calculating the real oxygen saturation value). The latter information may also be used to switch between certain physiological limits for the purpose of adapting and improving artifact suppression, e.g. minimum/maximum pulse rates for adults and neonates. Pulsations outside said limits (which are different for adults and neonates!) may be regarded as artefacts and therefore be suppressed.

According to preferred embodiments of the invention, encoding is performed either by conductive bridging members or an electrical impedance element, preferably a resistor, incorporated in the sensor. Other advantageous embodiments comprise a storage element, e.g. a ROM (read-only memory) or a customized integrated circuit, in the sensor.

The invention also relates to an oximeter for use with the medical sensor described above. This oximeter comprises decoding means responsive to the encoding means contained in the sensor. Signal processing is performed by the oximeter in dependence of the decoded signal as described above. Particularly, the decoded value may e.g. be used to directly calculate the real oxygen saturation value or to correct the theoretical value.

BRIEF DESCRIPTION OF THE DRAWINGS

The invention will now be described in detail, with reference to the accompanying drawings in which preferred embodiments of the invention are shown. In the drawings.

DETAILED DESCRIPTION OF THE INVENTION

Figure 1:
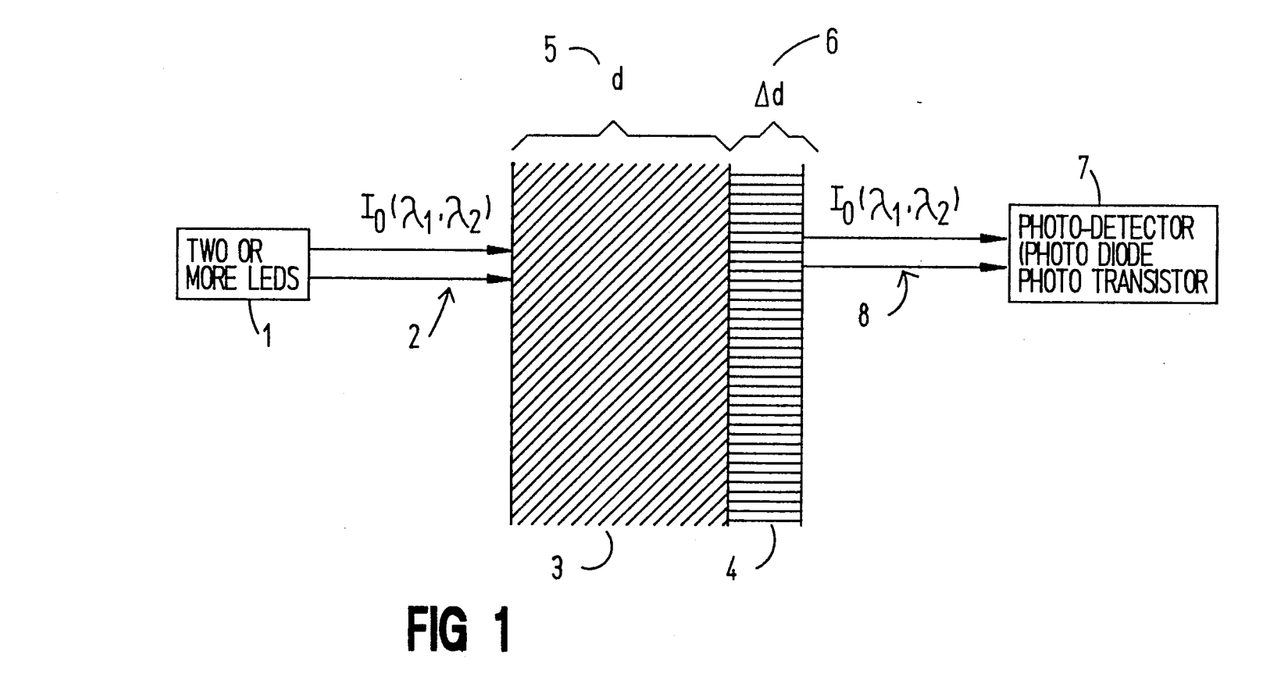
FIG. 1 depicts a schematic diagram of the technique of oxygen saturation.

In the schematic diagram of FIG. 1, reference no. 1 represents two or more light-emitting diodes (LEDs) of different wavelength $\lambda_1$, $\lambda_2$. The wavelenghts may e.g. be selected as 660 nm (Nanometers) and 950 nm. The light of these LEDs impinges on human tissue, e.g. a finger, with an original intensity $I_0(\lambda_1,\lambda_2)$ (reference no. 2).

The human tissue is represented by reference nos. 3 and 4. Ref. no. 3 represents the part of the tissue with constant absorbing characteristics and of homogeneous structure. Due to the constant absorption, the attenuation of the impinging light remains constant over time. Therefore, it is functionally equal to tissue of constant thickness d (ref. no. 5).

On the contrary, ref. no. 4 represents the pulsatile part of the arterial blood. Its thickness varies in dependence of the heartbeat and may therefore be represented by a varying thickness $\Delta d$ (ref. no. 6). It is evident that its absorption and therefore the attenuation of the light passing through it varies in the same manner.

The light is then received by a photodetector (photodiode, phototransistor) 7. Its intensity $I(\lambda_1,\lambda_2)$ (ref. no. 8) consists of a portion constant over time (tissue 3) and a time-varying portion (tissue 4).

It is understood, of course, that regions 3 and 4 of the tissue are in reality not arranged one after the other as shown in FIG. 1. Instead, FIG. 1 depicts merely a model of oxygen saturation measurement.

The shown technique is called "transmission technique" as transmitter and receiver are arranged on opposite sides of the tissue. According to another technique (not shown), they may also be arranged on the same side of the tissue. This technique is called "reflection technique" as the amount of reflected light is measured.

Figure 2A:
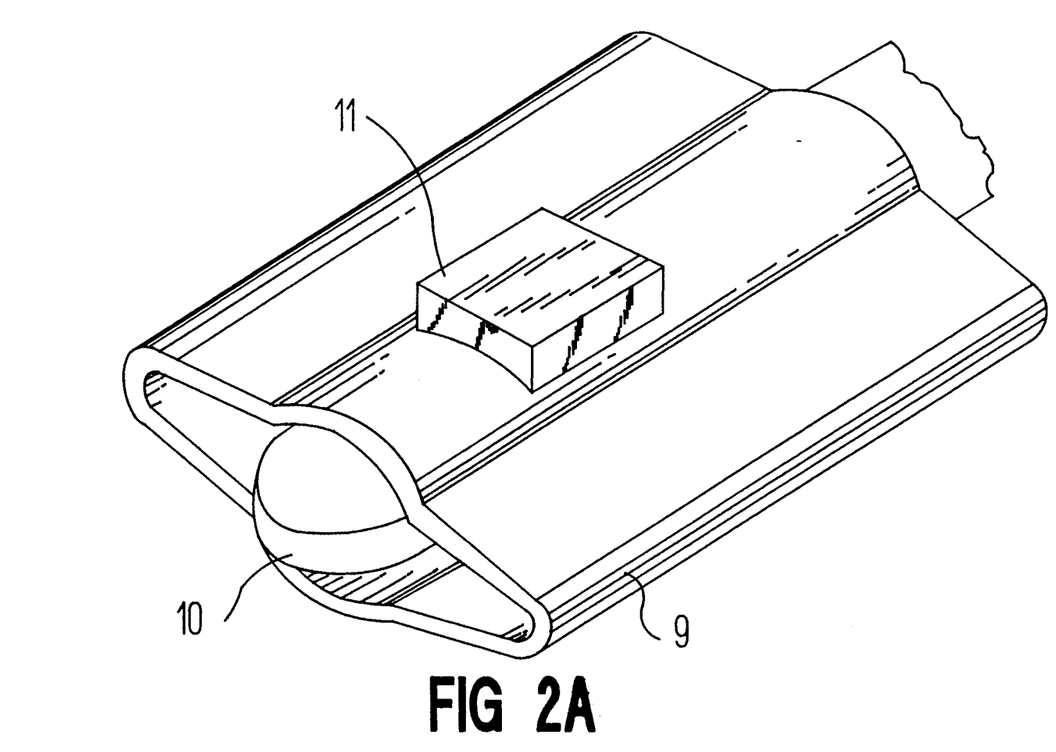
FIGS. 2a and 2b depict a typical sensor for application to a finger.

Transmitter and receiver are arranged in a sensor for application to a human being. FIG. 2a depicts, as an example, a sensor 9 for application to a human finger 10. Encapsulated in box 11 are two light-emitting diodes operated as transmitters. On the opposite side (not shown in FIG. 2a), a similar box contains the photoreceiver. The connection cables to the oximeter are not shown in FIG. 2a.

Figure 2B:
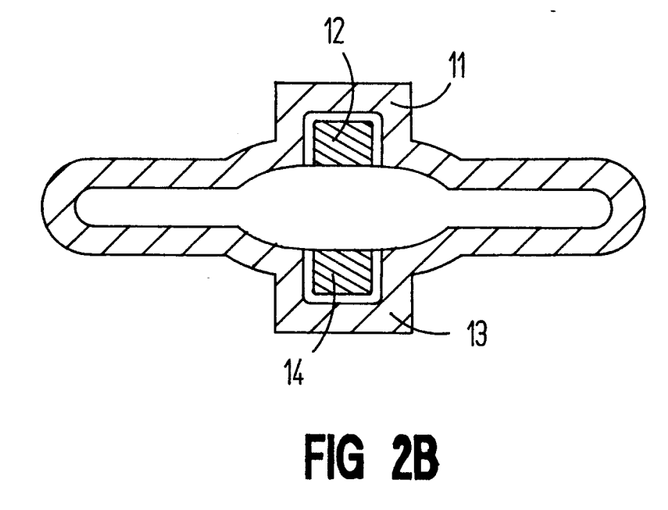

FIG. 2b shows a cross-section through sensor 9. It can be seen that box 11 contains transmitter diodes 12, and that box 13 contains the photoreceiver 14.

The sensor is detachably connected with an oximeter. According to Lambert-Beer's theory, the absorption of the tissue—expressed in the terms of the received intensity—can be used to calculate a "ratio". This ratio may be expressed in various mathematical terms, e.g. as described in EP-A-262 778, page 8, equation (10); U.S. Pat. No. 4,167,331, column 6, equation (11); WO 86/05674, page 36, line 23. It is directly related to the oxygen saturation value, at least in theory (see e.g. EP-A-262 778, page 3, line 50). In the present description, the ratio will be denominated as "R".

Figure 3:
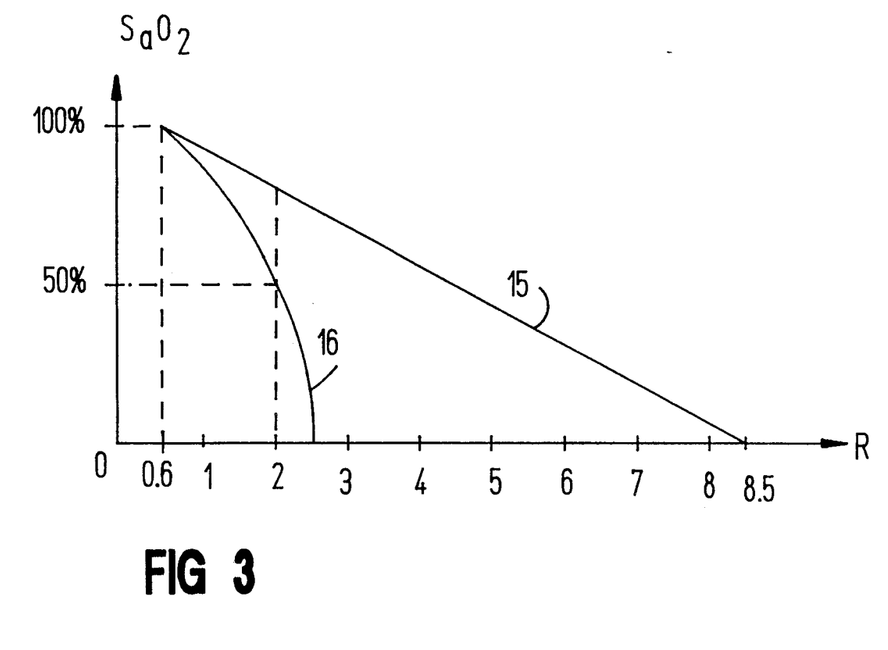
FIG. 3 shows the deviation between oxygen saturation values calculated according to the theory of Lambert-Beer and the real oxygen saturation values.

FIG. 3 depicts the relation between ratio R (horizontal axis) and oxygen saturation $SaO_2$ (vertical axis) for transmitter wavelenghts of $\lambda_1=660$ nm and $\lambda_2=950$ nm. Line 15 represents the relation according to Lambert-Beer's theory, whereas graph 16 depicts the relation in practice. It can be easily seen that, at least for a ratio R of more than 1, there is a significant deviation between the theoretical and the actual value. For an oxygen saturation of 50% (R=2), the actual value of the oxygen saturation is only 60% of the theoretical one.

Figure 4:
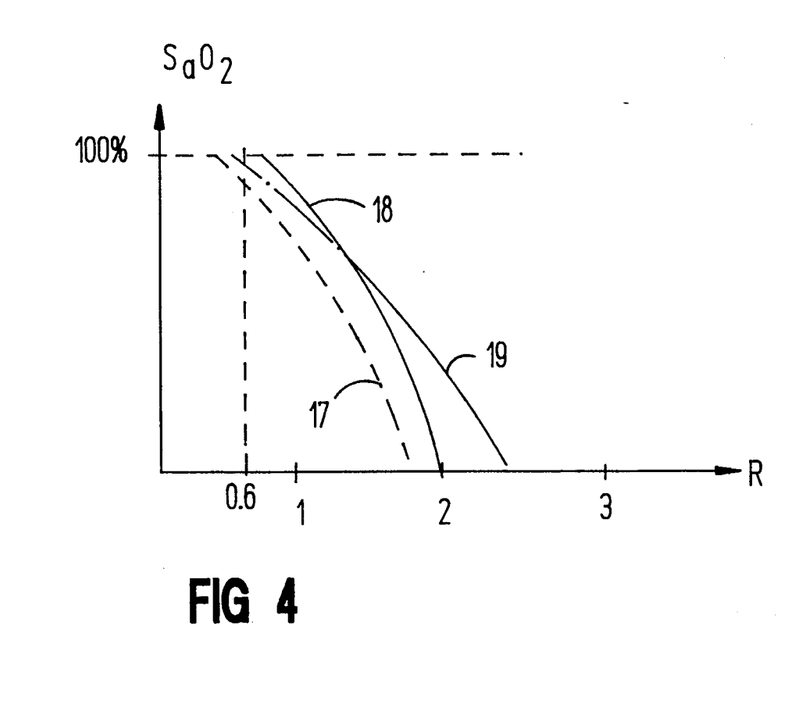
FIG. 4 depicts the dependence between oxygen saturation and the place of application of the sensor on an empirical basis.

Therefore, the oxygen saturation values calculated according to Lambert-Beer's theory have to be corrected on an empirical basis. According to the present invention, the kind of correction to be performed depends on the used sensor. FIG. 4 depicts the empirical correction for various kinds of sensors at transmitter wavelengths of 660 nm and 950 nm. The relation between ratio R and oxygen saturation (SaO₂) is shown for three different types of sensors (graphs 17,18,19). It is understood that, according to this invention, it is not mandatory to calculate first a theoretical oxygen saturation value and then to correct it in dependence on the decoded type of sensor. Instead, the real oxygen saturation value may also be calculated directly from ratio R and the decoded type of sensor, e.g. via reference tables contained in a memory.

Figure 5:
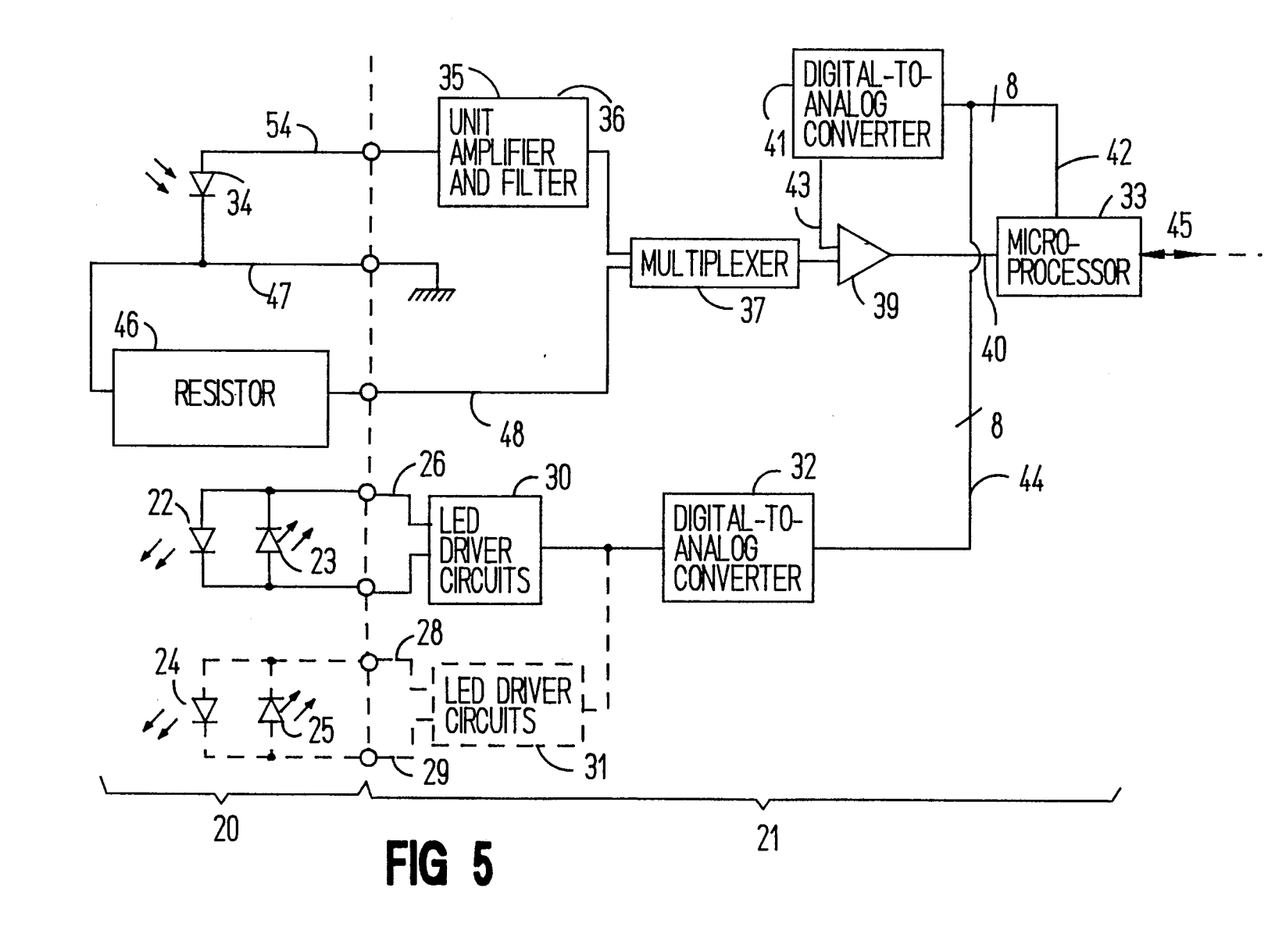
FIG. 5 depicts a simplified block diagram of an oximeter and a sensor therefor according to the present invention.

FIG. 5 depicts the basic components of an oximeter and a sensor therefor according to the present invention. The leftmost part of this figure—outlined as 20—shows the sensor and the rightmost part—outlined as 21—the oximeter.

The sensor comprises two light-emitting diodes 22 and 23 operated in counter-parallel. The wavelength of the emitted light is 660 nm (red) and 950 nm (infrared), respectively. The direction of the driving current determines the LED to be operated. Various types of sensors also comprise further transmitter LEDs as schematically indicated by LEDs 24 and 25, the connections of which are drawn in dashed lines.

The transmitter LEDs are connected with the oximeter as depicted by reference numbers 26, 27, 28 and 29. The oximeter comprises LED driver circuits 30 and 31 containing current sources. The driving current and its direction is determined by a digital-to-analog converter 32 under control of a microprocessor 33 (as will be described in detail below).

The sensor further comprises a photodetector (phototransistor or photodiode) 34. This photodetector may be arranged either opposite to the transmitter LEDs with respect to the human tissue (transmission measurement), or transmitter and receiver may be arranged adjacent to each other (reflection measurement). Photodetector 34 is connected with the oximeter via a line 54. (It has to pointed out that all lines connecting the sensor with the oximeter may be combined in one single cable!). The other pin of photodetector 34 is grounded (reference no. 47).

The signal generated by photodetector 34 is fed to unit 35 which comprises an amplifier as well as a filter. The signal is then fed (via line 36) to a multiplexer 37. For the purpose of determining the intensity of the received light, its output is connected (line 38) with a comparator 39, the output of which is further connected (reference number 40) with microprocessor 33. The microprocessor may apply a digital signal to digital-to-analog converter 41 (bus 42) which generates an analog signal. This analog signal (line 43) is also fed to comparator 39.

Microprocessor 33 applies sequentially increasing or decreasing digital signals to digital-to-analog converter 41. When comparator 39 changes its state, the unknown analog signal generated by photodetector 34 corresponds to the analog signal generated by digital-to-analog converter 41 and therefore to the digital signal generated by microprocessor 33. Digital-to-analog converter 41 and comparator 39 operate in basically known manner as an analog-to-digital converter using successive approximation.

Microprocessor 33 further controls digital-to-analog converter 32 (bus 44). Therefore, it determines the exciting current for LEDs 22–25 and consequently the intensity of the emitted light.

Line 45 indicates that the microprocessor may be further connected with a host processor, a display, a recorder and the like for displaying oxygen saturation, pulse, perfusion etc.

The sensor further comprises a resistor 46 connected to ground (line 47) and to multiplexer 37 (line 48). By selecting the appropriate input of multiplexer 37, the microprocessor may either determine the intensity of the received light or the resistance of resistor 46.

Resistor 46 is used to encode the sensor type. It has already been pointed out that sensors are e.g. available for application to the ear (adults)
the finger (adults)
the ridge of the nose (adults)
the foot (neonates)
the toe (neonates or adults)
the hand or arm (neonates)

and using either the transmission or the reflection technique. Further, the various sensors may comprise different numbers of transmitter LEDs. All of this information may be encoded in resistor 46. Only for the purpose of illustration, an encoding scheme is shown here:

| Type of Sensor | Resistance |
| --- | --- |
| Finger Sensor | |
| Transmission | 1 kOhm |
| for adults | |
| 2 transmitter LEDs | |
| Ear Sensor | |
| Transmission | 2 kOhms |
| for adults | |
| 2 transmitter LEDs | |
| Ear Sensor | |
| Transmission | 3 kOhms |
| for adults | |
| 3 LEDs | |
| Foot Sensor | |
| Transmission | 4 kOhms |
| for neonates | |
| 4 transmitter LEDs | |
| Arm Sensor | |
| Reflection | 5 kOhms |
| for neonates | |
| 2 transmitter LEDs | |

The microprocessor uses this information for selection among various correction algorithms or constants to calculate a highly accurate oxygen saturation value. Preferably, the microprocessor may have access to a reference table where the relation between ratio R and oxygen saturation SaO₂ is listed for each particular case (cf. FIG. 4). It is therefore possible to calculate the real oxygen saturation value directly from ratio R and the decoded type of sensor. Further, microprocessor 33 may perform further filter and signal processing tasks. It is also possible to perform the correction of the theoretical oxygen saturation value not in microprocessor 33, but in the host processor (not shown) instead. In this case, the resistance of resistor 46 or a code therefore has to be transmitted to the host processor.

It is understood that the indication of the sensor type does implicitly contain information on the place (part of the human body) where the sensor is applied.

The encoded information as described above may advantageously be used for further purposes. These are particularly:

1. The maximum exciting current of the transmitter LEDs may be adapted to the sensor in use. For example, for a first sensor of a certain type the maximum LED currents may be 80 mA for the red LED and 50 mA for the infrared LED, whereas for a second sensor of another type, the maximum LED current may be 150 mA for both the red and the infrared LED.

2. The information on the sensor in use also implies the number of transmitter LEDs. When the signal response of the LEDs is tested to detect malfunction, the microprocessor can distinguish between sensors with 2,3,4,... LEDs. (If the inventive encoding technique is not provided, such a test cannot be performed as a bad signal response may be either the result of a defective LED, or the sensor may not have such a LED at all).

3. The contact between sensor and human tissue, i.e. sensor fastening, can be tested by means of an attenuation measurement and correctly been interpreted. This is important as different sensors may have different attenuation characteristics. For example, in case of a transmission sensor, a high degree of attenuation indicates that sensor fastening is o.k., whereas a low degree of attenuation indicates bad contact. On the contrary, in the case of a reflection sensor, high attenuation indicates bad, and low attenuation good contact.

4. The information whether the sensor is an adult sensor or a neonatal sensor may be used to switch between certain physiological limits for the purpose of adaptation and improved artefact suppression. For example, in case of an adult, pulsations exceeding a pulse rate of 200 bpm (beats per minute) or falling below a pulse rate of 30 bpm may be rejected as artefacts. In case of a neonate, these limits are 350 bpm (high limit) and 50 bpm (low limit).

Figure 6:
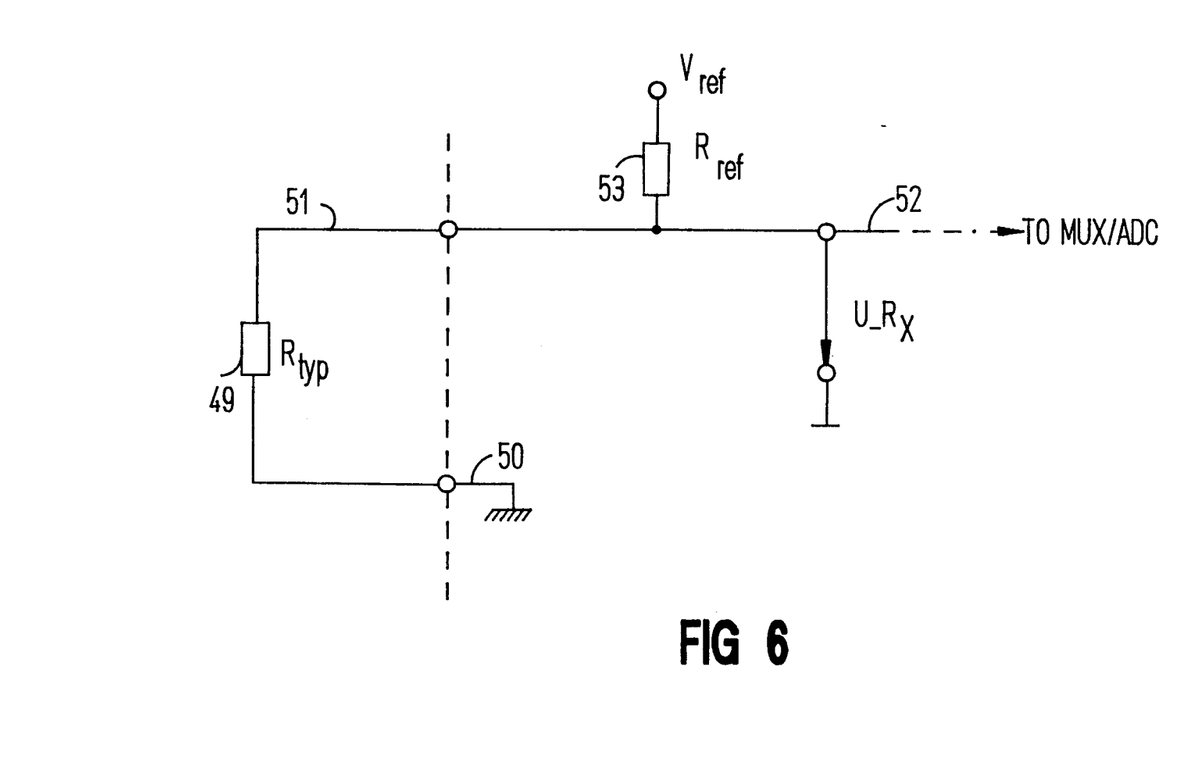
FIG. 6 shows a principal decoding circuit comprised in the oximeter if coding is done on the basis of a resistor.

FIG. 6 depicts the decoding means contained in the oximeter. Ref. no. 49 depicts the encoding resistor $R_{typ}$ of the sensor. This resistor is connected (line 50) with ground and (line 51) with the multiplexer/ analog-to-digital converter (ref. no. 52). Line 51 is connected, via reference resistor $R_{ref}$, with a reference voltage $V_{ref}$. Thus, voltage $U\_R_x$ can be used to determine the unknown resistance of resistor 49.

I claim:

1. An oximeter for use with a sensor that has means for emitting light when energized, means for producing identification signals uniquely representing the location on a patient's body at which the sensor is to be applied and means for producing information signals from which the oxygenization of blood may be determined in response to light impinging thereon, said oximeter comprising:
   means for supplying energy for said means for emitting light,
   means for supplying energy for said means for producing identification signals,
   means for receiving said information signals,
   means for receiving said identification signals,
   control means including means for processing received information signals in accordance with an algorithm selected in response to received identification signals, and
   said control means including means for carrying out an algorithm for determining whether or not said information signals result from a number of light emitting sources indicated by said sensor identification signals.

2. An oximeter for use with a sensor that has means for emitting light when energized, means for producing identification signals uniquely representing the location on a patient's body at which the sensor is to be applied and means for producing information signals from which the oxygenization of blood may be determined in response to light impinging thereon, said oximeter comprising:
   means for supplying energy for said means for emitting light,
   means for supplying energy for said means for producing identification signals,
   means for receiving said information signals,
   means for receiving said identification signals,
   control means including means for processing received information signals in accordance with an algorithm selected in response to received identification signals, and
   said control means including means for carrying out an algorithm for setting limits to results obtained from said information signals in response to said sensor identification signals.

3. Apparatus for determining the oxygenization of blood comprising:
   sensing means for transmitting light of different wavelengths, for producing data signals corresponding to the intensities of said wavelengths of light after they have passed through an intervening body and for providing an encoded signal indicative of the part of the body of a patient to which the sensor is adapted to be attached; and
   an oximeter coupled to receive said signals for determining the oxygenization of blood from said data signals in accordance with a method selected by said encoded signal.

* * * * *